(12) United States Patent
Ross

(10) Patent No.: US 11,344,267 B2
(45) Date of Patent: May 31, 2022

(54) PATIENT SUPPORT APPARATUS WITH X-RAY CASSETTE POSITIONING

(71) Applicant: Stryker Corporation, Kalamazoo, MI (US)

(72) Inventor: Ryan Ross, New Castle, IN (US)

(73) Assignee: Stryker Corporation, Kalamazoo, MI (US)

( * ) Notice: Subject to any disclaimer, the term of this patent is extended or adjusted under 35 U.S.C. 154(b) by 315 days.

(21) Appl. No.: 16/671,681

(22) Filed: Nov. 1, 2019

(65) Prior Publication Data

US 2020/0138389 A1 May 7, 2020

Related U.S. Application Data

(63) Continuation of application No. 62/754,633, filed on Nov. 2, 2018.

(51) Int. Cl.
*A61B 6/00* (2006.01)
*A61B 5/00* (2006.01)
*A61B 6/04* (2006.01)

(52) U.S. Cl.
CPC .............. *A61B 6/4283* (2013.01); *A61B 5/68* (2013.01); *A61B 6/04* (2013.01)

(58) Field of Classification Search
CPC ......... A61B 5/00; A61B 5/107; A61B 5/1072; A61B 5/1079; A61B 5/68; A61B 5/6887; A61B 5/6891; A61B 5/70; A61B 5/704; A61B 6/04; A61B 6/0407; A61B 6/0478; A61B 6/42; A61B 6/4283; A61B 6/44; A61B 6/4429; A61B 6/54; A61B 6/545; A61B 6/547; A61B 6/587; A61B 34/20; A61B 50/33; A61B 2034/2046; A61B 2034/2055; A61B 2034/2057; A61B 2034/2063; A61B 2560/02; A61B 2560/04; A61B 2560/0406; A61B 2560/0456; A61B 2560/0467; A61B 2562/16; A61B 2562/164; A61B 2562/17; A61G 13/00; A61G 13/10; A61G 13/101; A61G 2210/50; G01N 2223/30; G01N 2223/321; G01N 2223/50; H01J 37/20; H01J 2237/20; H01J 2237/2007; H01J 2237/202; H01J 2237/20292; H01J 2237/24415; H01L 27/144; H01L 27/146; H01L 27/14601;

(Continued)

(56) References Cited

U.S. PATENT DOCUMENTS 3,826,922 A 7/1974 Ingles
4,651,364 A 3/1987 Hayton et al.
(Continued)

*Primary Examiner* — Anastasia Midkiff
(74) *Attorney, Agent, or Firm* — Howard & Howard Attorneys PLLC

(57) ABSTRACT

A patient support apparatus includes a frame supporting a surface for a patient to lie on and an X-ray cassette mover coupled to the frame under the surface of the patient and adapted to receive an X-ray cassette. The patient support apparatus also includes one or more sensors located along the frame to sense a position of the patient on the surface and a controller in communication with the sensors and the X-ray cassette to determine the position of the patient on the surface and to position the X-ray cassette mover relative to the patient. The X-ray cassette mover provides a direct reference to the position of the X-ray cassette under the surface of the patient.

18 Claims, 6 Drawing Sheets

(58) Field of Classification Search
CPC ......... H01L 27/14618; H01L 27/14625; H01L 27/14658; H01L 27/14676
See application file for complete search history.

(56) References Cited

U.S. PATENT DOCUMENTS

| | | | |
|---|---|---|---|
| 4,665,574 A | 5/1987 | Filips et al. | |
| 4,916,725 A | 4/1990 | Quinter et al. | |
| 6,811,311 B2 | 11/2004 | Hayes et al. | |
| 6,862,762 B1 | 3/2005 | Johnson et al. | |
| 2005/0117709 A1* | 6/2005 | Dippl | G03B 42/02 378/189 |
| 2009/0060127 A1* | 3/2009 | Ohta | A61B 6/00 378/51 |
| 2010/0080360 A1* | 4/2010 | Ohta | A61B 6/56 378/209 |
| 2011/0110494 A1* | 5/2011 | Lee | A61B 6/4494 378/98 |
| 2013/0111664 A1 | 5/2013 | Childs et al. | |
| 2016/0015353 A1* | 1/2016 | Kim | A61B 6/405 378/69 |
| 2018/0085075 A1* | 3/2018 | Zemanek | A61B 6/0487 |
| 2018/0214092 A1* | 8/2018 | Nakayama | A61B 6/4283 |

* cited by examiner

PATIENT SUPPORT APPARATUS WITH X-RAY CASSETTE POSITIONING

CROSS-REFERENCE TO RELATED APPLICATION

The subject patent application claims priority to and all the benefits of U.S. Provisional Patent Application No. 62/754,633 filed on Nov. 2, 2018, the disclosure of which is hereby incorporated by reference in its entirety.

BACKGROUND

Currently hospitals require one or two caregivers to manually move the patient to place an X-ray cassette behind the patient's back for a chest X-ray. This typically occurs daily in an intensive care unit (ICU) of a health care facility and can become a huge strain on the caregivers based on positioning the X-ray cassette while moving the patient up and over out of the way of the cassette placement. Besides the strain on caregivers this also includes wear and tear in the form of mattress cover tears or damaged X-ray cassettes from the amount of force required to insert the cassette behind the patient's back.

A patient support apparatus for handling X-ray cassettes is desired that addresses one or more of the aforementioned challenges.

DETAILED DESCRIPTION

Figure 1:
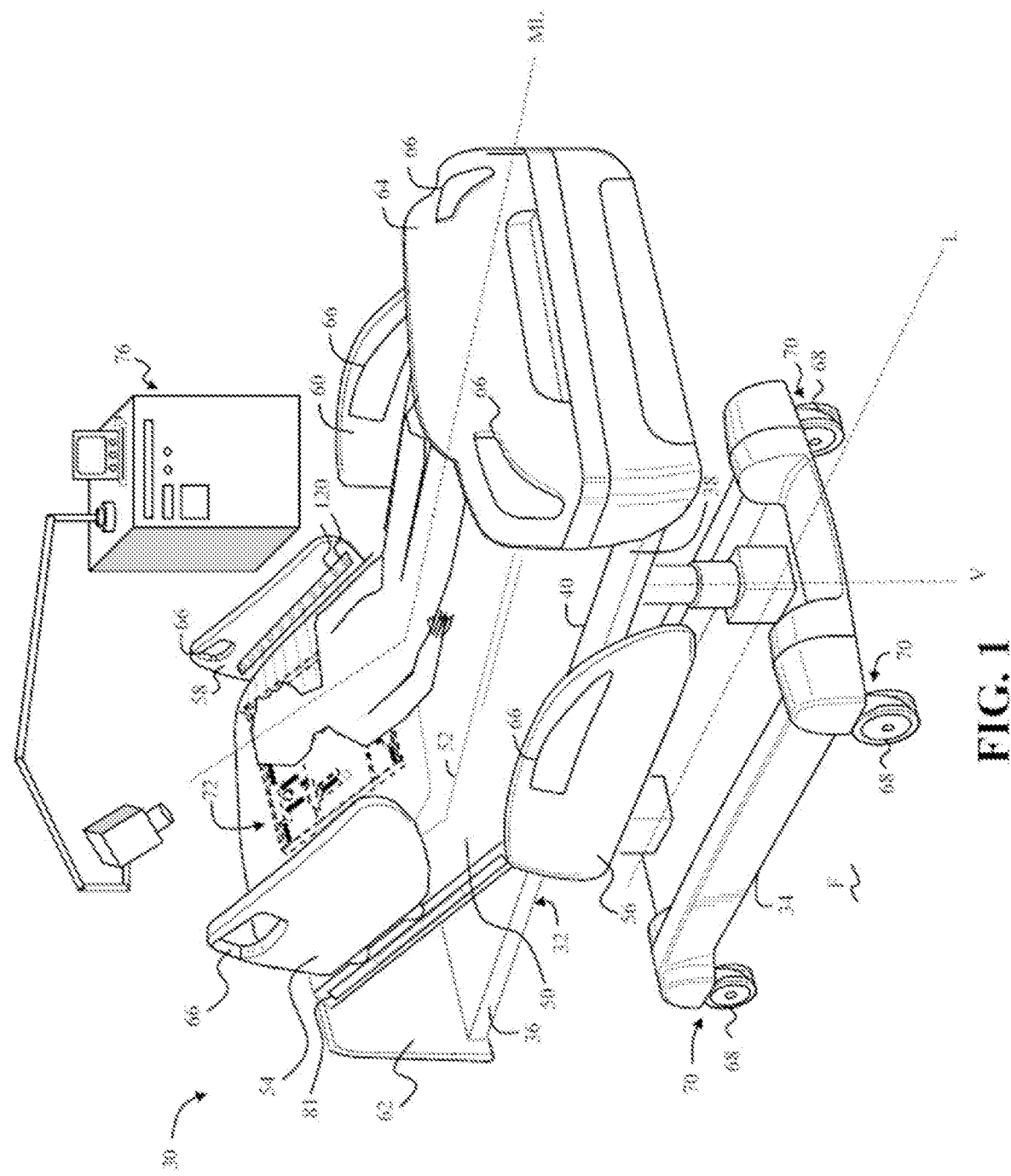
FIG. 1 is a perspective view of a patient support apparatus with an X-ray cassette mover and X-ray cassette and having a patient thereon.

Referring to FIG. 1, a patient support apparatus 30 is shown for supporting a patient in a health care setting. The patient support apparatus 30 illustrated in FIG. 1 comprises a hospital bed. In other embodiments, however, the patient support apparatus 30 may comprise a stretcher, cot, wheelchair, chair, or similar apparatus utilized in the care of a patient.

The patient support apparatus 30 includes a support structure, generally indicated at 32, providing support for the patient. The support structure 32 illustrated in FIG. 1 comprises a base 34 and a support frame 36 disposed above the base 34 and supported by the base 34. The support structure 32 also comprises a patient support deck 38 disposed on the support frame 36. The patient support deck 38 comprises sections, some of which are capable of articulating (e.g., pivoting) relative to the support frame 36. The patient support deck 38 provides a patient support surface 40, upon which the patient is supported.

The patient support apparatus 30 also includes a mattress 50 disposed on the patient support deck 38 during use. The mattress 50 comprises a secondary patient support surface 52 upon which the patient is supported. The mattress 50 may be omitted in certain embodiments, such that the patient rests directly on the patient support surface 40. The base 34, support frame 36, patient support deck 38, and patient support surfaces 40, 52, each comprise a head end and a foot end corresponding to designated placement of the patient's head and feet on the patient support apparatus 30. The base 34 comprises a longitudinal axis L along its length from the head end to the foot end. The base 34 also comprises a vertical axis V arranged crosswise (e.g., perpendicularly) to the longitudinal axis L along which the support frame 36 is lifted and lowered relative to the base 34. The patient also has a midline axis ML. The construction of the support structure 32 may take on any known or conventional design, and is not limited to that specifically set forth above. For example, the support structure 32 may be like that shown in U.S. Patent Application Pub. No. 2013/0111664 to Childs et al., filed on Aug. 14, 2012, entitled, "Wheeled Carriage With Brake Lock System," which is hereby incorporated herein by reference.

The patient support apparatus 30 may include patient barriers, such as side rails 54, 56, 58, 60 coupled to the support frame 36 and/or patient support deck 38 and are thereby supported by the base 34. If the patient support apparatus 30 is a stretcher or a cot, there may be fewer side rails.

The patient support apparatus 30 may include a headboard 62 and a footboard 64 coupled to the support frame 36. The headboard 62 and footboard 64 may be coupled to any location on the patient support apparatus 30, such as the support frame 36 or the base 34.

The patient support apparatus 30 may include caregiver interfaces 66, such as handles, shown integrated into the footboard 64 to facilitate movement of the patient support apparatus 30 over a floor surface F. Additional caregiver interfaces 66 may be integrated into other components of the patient support apparatus 30, such as the headboard 62 or the side rails 54, 56, 58, 60. The caregiver interfaces 66 are graspable by the caregiver to manipulate the patient support apparatus 30 for movement, and the like. Other forms of the caregiver interface 66 are also contemplated.

Figure 2:
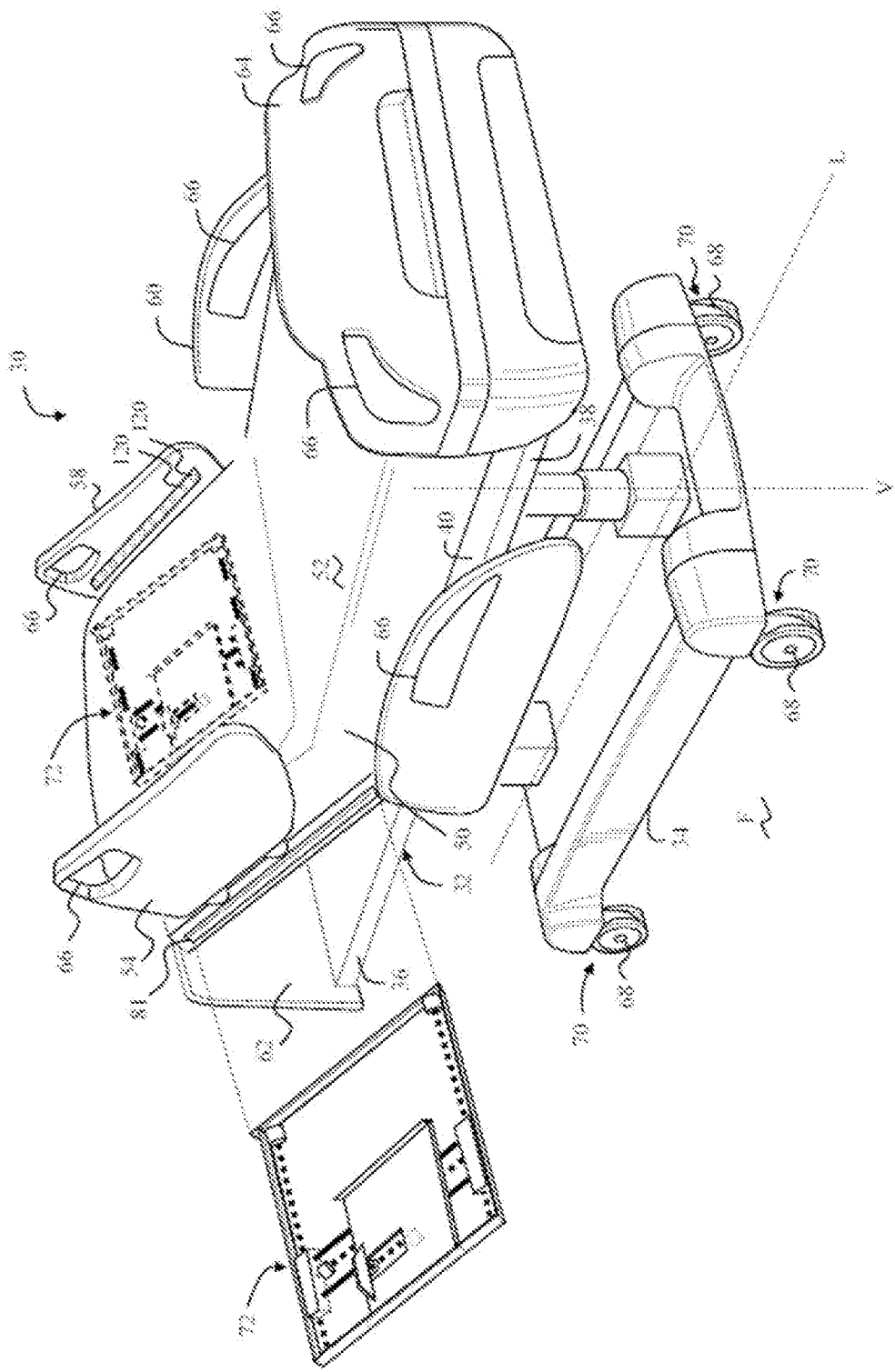
FIG. 2 is a perspective view of the patient support apparatus of FIG. 1 with the X-ray cassette mover in both phantom and exploded view with the patient removed.

Referring to FIGS. 1 and 2, the patient support apparatus 30 further includes a plurality of wheels 68 coupled to the base 34 to facilitate transport over the floor surface F. The wheels 68 are arranged in each of four quadrants of the base 34 adjacent to corners of the base 34. In the embodiment shown, the wheels 68 are caster wheels able to rotate and swivel relative to the support structure 32 during transport. Each of the wheels 68 forms part of a caster assembly 70. Each caster assembly 70 is mounted to the base 34. Additional wheels are also contemplated. For example, the patient support apparatus 30 may comprise four non-powered caster wheels 68, along with one or more powered wheels. It should be appreciated that although the caster assembly 70 is shown and described as being part of the patient support apparatus 30, the caster assembly 70 could be used with any mobility apparatus in which caster wheels are suitable for providing mobility.

Figure 3:
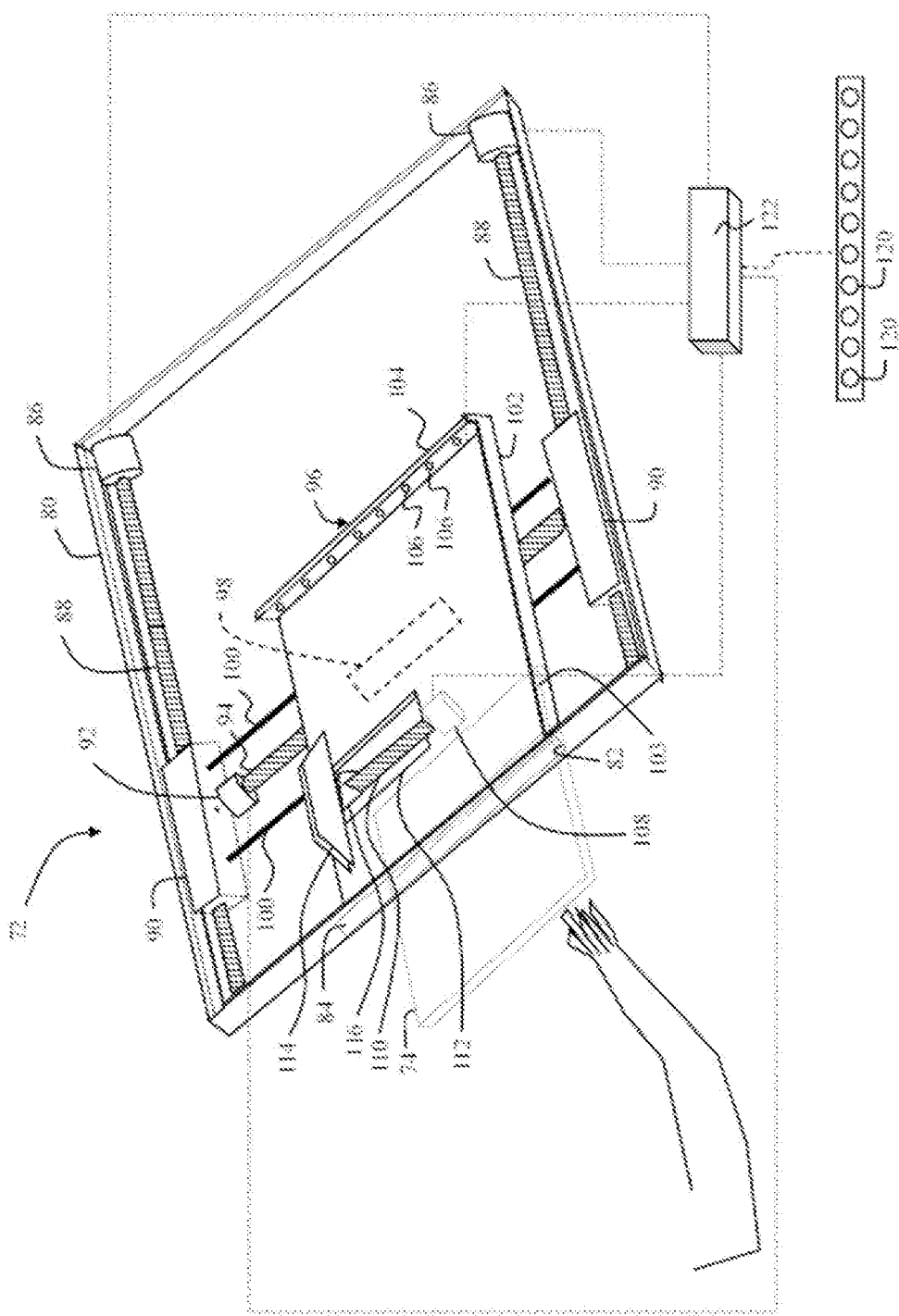
FIG. 3 is a perspective view of the X-ray cassette mover of FIGS. 1 and 2 with the X-ray cassette illustrated being loaded into the X-ray cassette mover.
Figure 4:
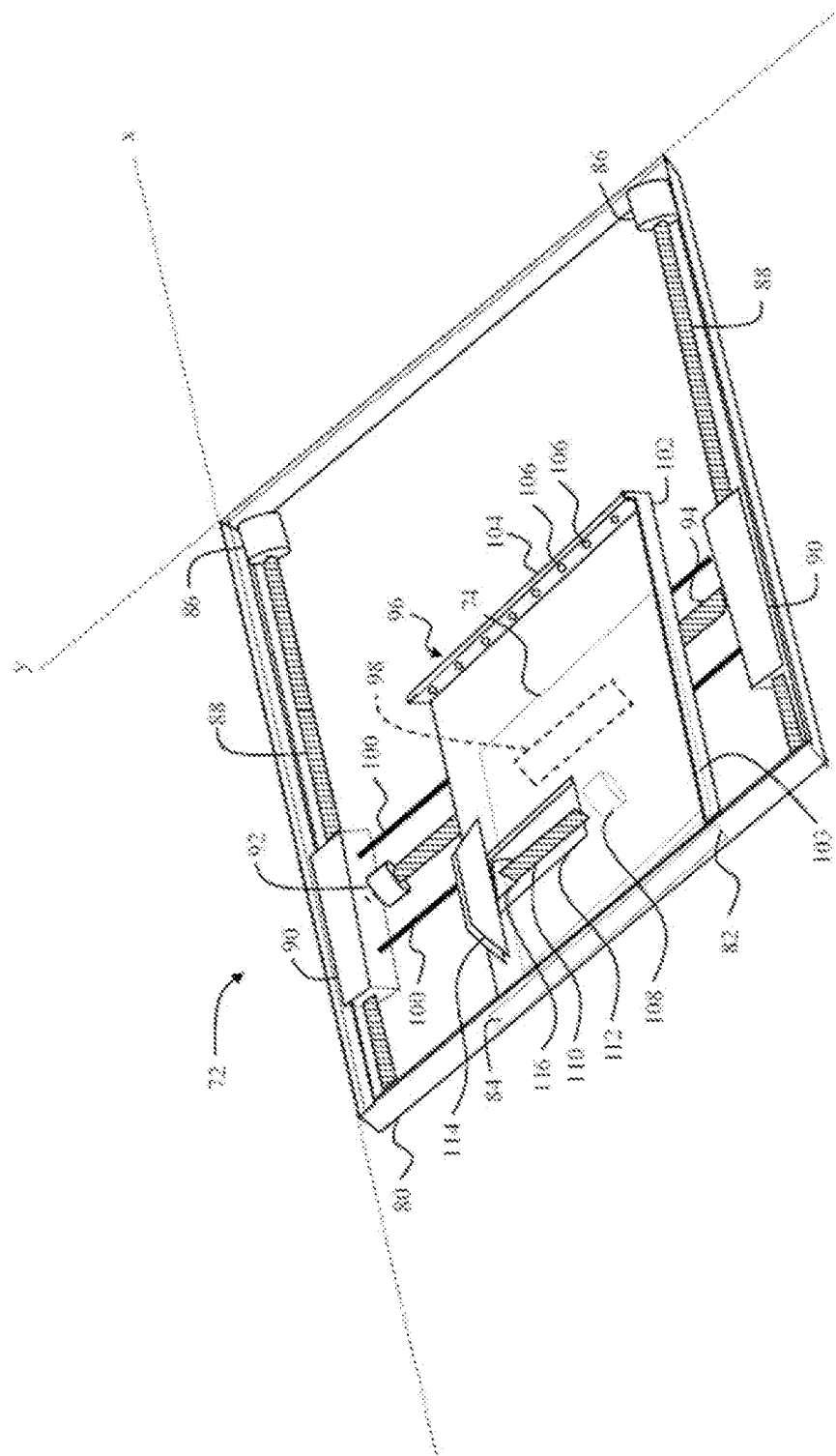
FIG. 4 is a perspective view of the X-ray cassette mover of FIG. 3 with the X-ray cassette in a first operational position.
Figure 5:
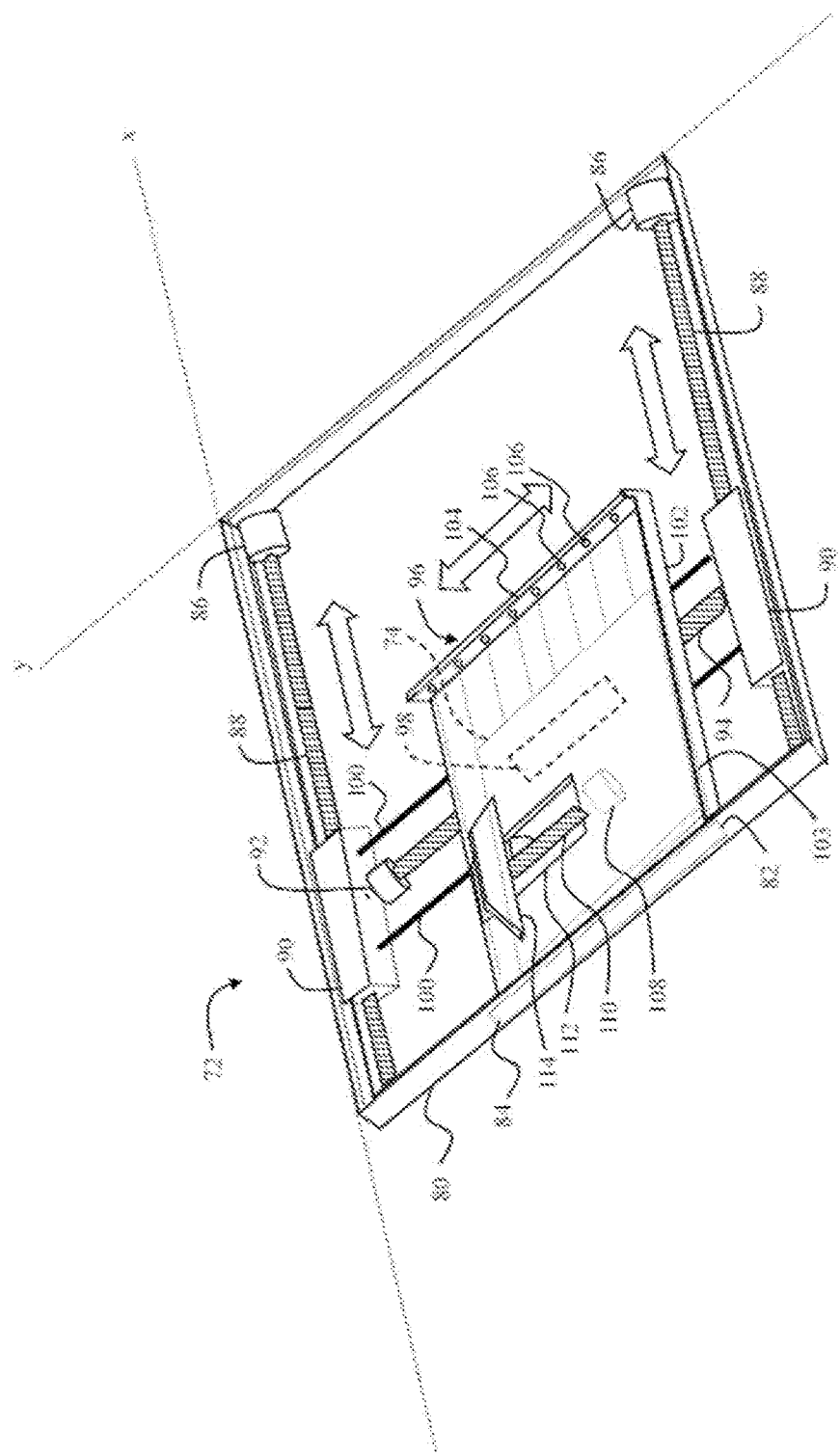
FIG. 5 is a perspective view of the X-ray cassette mover of FIG. 3 with the X-ray cassette in a second operational position.

The patient support apparatus 30 also includes an X-ray cassette mover, generally indicated at 72, coupled to the support frame 36 underneath the patient support surface 40 of the patient support deck 38. The X-ray cassette mover 72 is disposed in the patient support deck 38. As illustrated in FIGS. 3-5, the X-ray cassette mover 72 receives and supports an X-ray cassette 74 to allow an X-ray to be taken of the patient. As illustrated in FIGS. 1 and 2, an X-ray machine or device 76 may be used in conjunction with the patient support apparatus 30 to take an X-ray of a portion of the patient, for example the lungs, in the health care setting. It should be appreciated that the patient support deck 38 is made of a material to allow X-rays from the X-ray device 76 to pass therethrough. It should also be appreciated that the X-ray device 76 is known in the art.

Referring to FIGS. 3-5, one embodiment of the X-ray cassette mover 72 is shown. In this embodiment, the X-ray cassette mover 72 includes a mover frame 80 coupled to the patient support deck 38. As illustrated in FIGS. 1 and 2, the mover frame 80 may be disposed through an opening 81 in the patient support deck 38 and disposed therein. In one embodiment, the mover frame 80 is generally rectangular in shape, but may be any suitable shape. The mover frame 80 includes an opening or slot 82 to allow the X-ray cassette 74 to be loaded and unloaded therein. In one embodiment, the slot 82 is located on a side thereof and generally rectangular in shape, but may be any suitable shape to allow insertion of the X-ray cassette 74. The mover frame 80 may include a door 84 pivotally hinged thereto to open and close the slot 82. In one embodiment, the door 84 is generally rectangular in shape, but may be any suitable shape to close the slot 82.

The X-ray cassette mover 72 also includes a pair of first actuators 86, for example electric motors, coupled to the mover frame 80 and a pair of rotatable first threaded lead screws 88 coupled to the first actuators 86 and the mover frame 80 and spaced laterally within the mover frame 80. In one embodiment, the first actuators 86 are disposed along and inside on the side of the mover frame 80 opposite the side with the slot 82 and connected to the mover frame 80 by a suitable mechanism such as fasteners (not shown). The first threaded lead screws 88 have one end rotatably coupled to the first actuators 86 and extend longitudinally from the first actuators 86. The other end of the first threaded lead screws 88 are rotatably connected to the side of the frame mover 80 by a suitable mechanism such as journals (not shown).

The X-ray cassette mover 72 also includes a pair of first threaded support nuts 90 disposed along and coupled to the first threaded lead screws 88. In one embodiment, each of the first threaded support nuts 90 is disposed about and threadably engages one of the first threaded lead screws 88 for moving along the first threaded lead screws 88 when rotated. In one embodiment, the first threaded support nut 90 is generally rectangular in shape, but may be any suitable shape to move along the first threaded lead screw 88.

The X-ray cassette mover 72 further includes a second actuator 92, for example an electric motor, coupled to one of the first threaded support nuts 90 and a rotatable second threaded lead screw 94 coupled to and extending laterally between the second actuator 92 and the other one of the first threaded support nuts 90. In one embodiment, the second actuator 92 is disposed along and inside on a side of the first threaded support nut 90 and connected to the first threaded support nut 90 by a suitable mechanism such as fasteners (not shown). The second threaded lead screw 94 has one end rotatably coupled to the second actuator 92 and extends laterally from the second actuator 92. The other end of the second threaded lead screw 94 is rotatably coupled to the other first threaded support nut 90 by a suitable mechanism such as a journal (not shown).

The X-ray cassette mover 72 also includes a support tray, generally indicated at 96, to support the X-ray cassette 74 and a second threaded support nut 98 coupled to the support tray 96 and threadably engaging the second threaded lead screw 94 for moving along the second threaded lead screw 94. In one embodiment, the support tray 96 is generally rectangular in shape, but may be any suitable shape to support the X-ray cassette 74. In one embodiment, the second threaded support nut 98 is disposed beneath the support tray 96 and fixed to the support tray 96. The second threaded support nut 98 is also disposed about and threadably engages the second threaded lead screw 94 for moving along the second threaded lead screw 98 when rotated. In one embodiment, the second threaded support nut 98 is generally rectangular in shape, but may be any suitable shape to support the support tray 96 and move along the second threaded lead screw 94.

The X-ray cassette mover 72 further includes a pair of support rods 100 extending laterally between the first threaded support nuts 90 to support movement of the support tray 96. In one embodiment, the support rods 100 are spaced longitudinally and have one end connected to one of the first threaded support nuts 90 and another end connected to the other one of the first threaded support nuts 90. It should be appreciated that the X-ray cassette mover 72 moves the support tray 96 via the actuators 86 and 92, threaded lead screws 88 and 94, and threaded support nuts 90 and 98 longitudinally and laterally relative to the mover frame 80 as illustrated in FIG. 5.

In one embodiment, the support tray 96 includes a base member 102 to support the X-ray cassette 74 and a back member 104 to act as a stop for the X-ray cassette 74. In one embodiment, the base member 102 is generally rectangular in shape, but may be any suitable shape to support the X-ray cassette 74. The base member 102 is connected to the second threaded support nut 98 by a suitable mechanism such as fasteners (not shown). In one embodiment, the back member 104 is generally rectangular in shape, but may be any suitable shape to act as a stop for insertion of the X-ray cassette 74. The support tray 96 may include one or more cassette sensors 106 disposed laterally along the back member 104 to sense or detect a size of the X-ray cassette 74 loaded or disposed on the base member 102. In one embodiment, the sensors 106 may be of a Hall effect type to detect a size of the X-ray cassette 74. It should be appreciated that there are different sizes of X-ray cassettes 74.

The support tray 96 also includes a third actuator 108, for example an electric motor, coupled to the base member 102 and a rotatable third threaded lead screw 110 extending laterally from the third actuator 108. In one embodiment, the third actuator 108 is disposed beneath the base member 102 and connected to the base member 102 by a suitable mechanism such as fasteners (not shown). The support tray 96 includes a recess 112 extending laterally along and into the base member 102 and the third lead screw 110 extends into the recess 112. In one embodiment, the recess 112 is generally rectangular in shape, but may be any suitable shape. The support tray 96 further includes a clamp 114 coupled to the third threaded lead screw 110 to move and engage and disengage the X-ray cassette 74. In one embodiment, the clamp 114 is generally parallelogram shaped, but may be any suitable shape to engage the X-ray cassette 74. The clamp 114 extends longitudinally and has a threaded nut portion 116 disposed in the recess 112. The threaded nut portion 116 is also disposed about and threadably engages the third threaded lead screw 110 for movement along the recess 112 and the third threaded lead screw 110.

As illustrated in FIGS. 1 and 2, the patient support apparatus 30 includes one or more patient sensors 120 coupled to each of the patient barriers such as side rails 54 and 58 to determine a position of the patient vertically on the patient support deck 38 and a position horizontally on the patient support deck 38, such as a position of one or more of the patient's head, neck, and torso. In one embodiment, the sensors 120 comprise at least one of ultrasonic sensors, laser sensors, and distance sensors. In one embodiment, the sensors 120 are spaced longitudinally along the side rails 54 and 58. As illustrated in FIG. 3, the patient support apparatus 30 also includes a controller 122 coupled to and in communication with the sensors 120 and the X-ray cassette mover 72. As illustrated, the controller 122 is also coupled to and in communication with the actuators 86, 92, 108 and the sensors 106.

In one embodiment, the controller 122 uses data from the sensors 106 on the support tray 96 to automatically determine a size of the X-ray cassette 74. For example, the size of the X-ray cassette 74 can be determined by measuring the x, y dimensions (width and height) of the X-ray cassette 74 using position data. In one implementation, an x-dimension of the X-ray cassette 74 can be determined by the controller 122 using the sensors 106 to indicate the distance of the X-ray cassette 74 from the back member 104, e.g., the gap between the X-ray cassette 74 and the back member 104, as shown in FIG. 5. Assuming that the X-ray cassette 74 has been pushed completely into the slot 82 so that one edge of the X-ray cassette 74 is adjacent to the slot 82, and knowing the distance of the gap between the X-ray cassette 74 and the back member 104 via the sensors 106 (which are arranged parallel to the y-axis to measure distances in the x-dimension), the controller 122 can determine the x-dimension of the X-ray cassette 74. The y-dimension could also be determined by the controller 122 using measurements from the sensors 106. For example, as shown in FIG. 5, if enough sensors 106 are provided along the back member 104 so that some of the sensors 106 detect an edge of the X-ray cassette 74, while others do not (note that one sensor 106 does not detect the edge in FIG. 5), the controller 122 can determine the y-dimension based on the number of the sensors 106 that detect the edge, i.e., via a known distance between the outermost of the sensors 106 that detect the edge, thus indicating the y-dimension. In another implementation, encoder data or position data from any suitable position sensor, such as an encoder in the actuator 108 or a linear potentiometer attached to the clamp 114 and/or the base member 102, can indicate a position of the clamp 114 along the third threaded lead screw 110 of the X-ray cassette 74 and relative to a side wall 103 against which the clamp captures the X-ray cassette 74. Accordingly, a y-dimension of the X-ray cassette 74 can be determined by the controller 122 using the data provided by the position sensor.

The controller 122 includes a processor (not shown) having an algorithm to center the X-ray cassette 74, for example on lungs of the patient. In one embodiment, the controller 122 uses data from the sensors 120 to calculate a current position of the patient relative to the frame 36 so that the controller 122 is able to determine a desired placement of the X-ray cassette 74 based on the determined size of the X-ray cassette 74. In one embodiment, the controller 122 activates the X-ray mover 72 to move the support tray 96 to center the X-ray cassette 74 on lungs of the patient using the data from the sensors 120. It should be appreciated that there is a gap defined between the patient barriers such as side rails 54 and 58 and the patient support deck 38 such that a home position of the support tray 96 and X-ray cassette 74 is adjacent the gap. It should also be appreciated that the sensors 120 provide data as to whether the patient is off center relative to the patient support deck 38 for the calculation to move the support tray 96 and X-ray cassette 74 to center on the lungs of the patient. It should further be appreciated that once the support tray 96 and X-ray cassette 74 are in position relative to the patient, the X-ray device 76 operates or is operated.

Operation of the X-ray cassette mover 72 is illustrated in FIGS. 3-5. Notably, an operator's hand loads the X-ray cassette 74 into the cassette mover 72 by pushing the X-ray cassette 74 through the slot 82 in the mover frame 80 and upon the support tray 96 as illustrated in FIG. 3. In FIG. 3, the controller 122 uses data from the sensors 106 to determine the size of the X-ray cassette 74. In FIG. 4, the support tray 96 is shown in its initial position with respect to the cassette mover 72 with the X-ray cassette 74 being in the loaded position. In FIG. 5, the controller 122 activates the third actuator 108 to rotate the third threaded lead screw 110 to move and pull the clamp 114 down to engage the X-ray cassette 74. It should be appreciated that the controller 122 may determine that the X-ray cassette 74 is sufficiently clamped down by increased current to the third actuator 108 being sensed by the controller 122.

Thereafter, if necessary, the X-ray cassette mover 72 moves the support tray 96 and X-ray cassette 74 to the home position previously described and shown in FIGS. 3-5. The controller 122 receives data from the sensors 120 and moves the support tray 96 and X-ray cassette 74 to position the X-ray cassette 74 under the anatomy of the patient lying upon the patient support apparatus 30. It should be appreciated that the X-ray cassette 74 is fixed relative to the cassette mover 72. It should also be appreciated that the controller 122 uses x-y coordinates as illustrated in FIGS. 4 and 5, or other suitable positioning methods, to position the X-ray cassette 74 relative to the patient.

In one implementation, the sensors 120 shown in FIG. 2 are placed at predefined locations in the x-y coordinate system. Additionally, although only one set of sensors 120 is shown mounted to the side rail 58 in FIG. 2, an opposing set of sensors 120 may be located on the opposite side rail 54. In this way, the sensors 120 can detect an approximate x, y position of the patient, and the anatomy of interest, in the x-y coordinate system. For example, the sensors 120 on the side rails 54, 58 may be arranged parallel to the y-axis to detect distances in the x-dimension and thereby detect a plurality of distances (e.g., using ultrasonic sensors) from the sensors 120 to the patient. Assuming a general symmetry of the patient lying on the mattress 50, the controller 122 approximates a placement of the patient with respect to the x-axis of the x-y coordinate system, e.g., the patient is centrally positioned between the side rails 54, 58, or the patient is offset from center. The controller 122 determines a location of the midline axis ML of the patient by comparing the measurements taken by the sensors 120 and approximating an x-dimension location of the midline axis ML, parallel to the y-axis.

Similarly, the sensors 120 can approximate the location of the patient or patient's anatomy on the y-axis. By knowing the distance between opposing sensors 120 on the side rails 54, 58 (e.g., the width between the side rails 54, 58), and given the measurements from the sensors 120, which detect an outer surface of the patient (skin, clothes, etc.), the width of the patient is calculated by the controller 122 as the width between opposing sensors 120 minus the detected distances to the patient (on both sides of the patient). This calculated width can then be compared by the controller 122 to a look-up table that correlates widths to patients and/or patient anatomy. For example, given calculated widths of 8-15 inches, the look-up table may indicate that the sensors 120 have located the patient's head, for widths of 20-40 inches the look-up table may indicate that the sensors 120 have located the patient's torso, and so on. Based on these determinations, and given statistical data of the location of a normal or average person's lungs relative to their head and/or torso locations, the controller 122 can then approximate an x-y location of the patient's lungs in the x-y coordinate system. In other versions, the patient's weight and/or height may also be considered and input to the controller 122 to better approximate the location of the patient's lungs. The controller 122 can then instruct the X-ray cassette mover 72 to locate the X-ray cassette 74 directly beneath the patient's lungs using the calculated x-y coordinates.

It should be appreciated that, after the x-ray images are acquired, the X-ray cassette mover 72 is moved back to the home position, which is used to receive and eject the X-ray cassette 74 from the X-ray cassette mover 72. Movement back to the home position may be manual or automated, and could be based on communication between the controller 122 and the X-ray device 76, i.e., once the image is acquired a signal from the X-ray device 76 to the controller 122 could trigger automated movement back to the home position.

Figure 6:
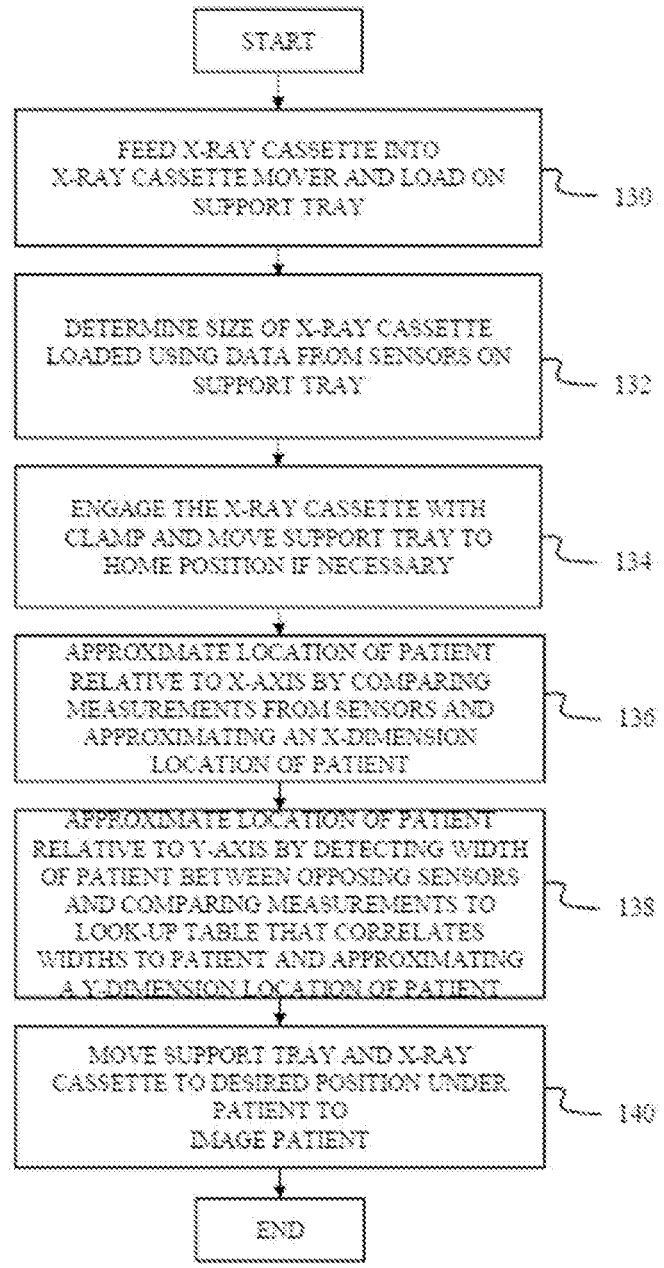
FIG. 6 is a flowchart of a method, according to the present invention, of moving the X-ray cassette with the X-ray cassette mover into an operational position relative to the patient.

Referring to FIG. 6, a method, according to the present invention, of moving the X-ray cassette 74 with the X-ray cassette mover 72 into an operational position relative to the patient is show. After the method starts, in block 130, the method includes the step of feeding the X-ray cassette 74 into the X-ray cassette mover 72 and loading the X-ray cassette 74 on the support tray 96. The method advances to block 132 and includes the step of determining the size of the X-ray cassette 74 loaded on the support tray 96 using data from the sensors 106 on the support tray 96. The method advances to block 134 and includes the step of engaging the X-ray cassette 74 with the clamp 114 and moving the support tray 96 to the home position if necessary. The method then advances to block 136 and includes the step of approximating the location of the patient on the patient support apparatus 30 relative to the x-axis of the x-y coordinate system by comparing measurements taken by the sensors 120 on the patient support apparatus 30 and approximating an x-dimension location of the patient. The method then advances to block 138 and includes the step of approximating the location of the patient on the patient support apparatus 30 relative to the y-axis of the x-y coordinate system by detecting the width of the patient with the sensors 120 on the patient support apparatus 30 and comparing measurements to a look-up table that correlates widths to the patient and approximating a y-dimension location of the patient. The method then advances to block 140 and includes the step of moving the support tray 96 and X-ray cassette 74 to a desired position under the patient to image the patient. The method then ends.

Accordingly, the present disclosures describes an automated system that uses proximity sensors 120 to identify the head, neck, and/or torso position of the patient in proximity to the side rails 54, 56, 58, 60. Using that data, the X-ray cassette 74 is fed into the slot 82 on the side of the X-ray cassette mover 72 directly beneath the patient support deck 38 where the controller 122 can analyze and determine the size of X-ray cassette 74 entered. Coupled with the size of the X-ray cassette 74 and the data from the sensors 120 as to the patient's position, the X-ray cassette mover 72 can mechanically move the X-ray cassette 74 to a desired position to image the lungs of the patient or any other desired position, depending on the part of the patient to be imaged.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support apparatus comprising:
a frame supporting a support surface for a patient to lie on;
an X-ray cassette mover coupled to the frame under the support surface and adapted to receive an X-ray cassette;
one or more patient position sensors to sense a position of the patient on the support surface; and
a controller in communication with the one or more patient position sensors and the X-ray cassette mover, the controller being configured to determine the position of the patient on the support surface based on information from the one or more patient position sensors, and to position the X-ray cassette mover relative to the patient based on the information from the one or more patient position sensors.

2. The patient support apparatus of claim 1, wherein the X-ray cassette mover comprises a mover frame and a slot in one side of the mover frame for allowing insertion and removal of the X-ray cassette.

3. The patient support apparatus of claim 2, wherein the X-ray cassette mover comprises a pair of first actuators coupled to and spaced within the mover frame and in communication with the controller.

4. The patient support apparatus of claim 3, wherein the X-ray cassette mover comprises a pair of first threaded lead screws having one end coupled to the first actuators and another end coupled to the mover frame.

5. The patient support apparatus of claim 4, wherein the X-ray cassette mover comprises a pair of first threaded support nuts, one of the first threaded support nuts threadably engaging one of the first threaded lead screws for moving the first threaded support nuts along the first threaded lead screws.

6. The patient support apparatus of claim 5, wherein the X-ray cassette mover comprises a second actuator coupled to one of the first threaded support nuts and in communication with the controller.

7. The patient support apparatus of claim 6, wherein the X-ray cassette mover comprises a second threaded lead screw having one end coupled to the second actuator and another end coupled to the other one of the first threaded support nuts.

8. The patient support apparatus of claim 7, wherein the X-ray cassette mover comprises a support tray and a second threaded support nut coupled to the support tray and threadably engaging the second threaded lead screw for moving along the second threaded lead screw.

9. The patient support apparatus of claim 8, wherein the support tray comprises a base member adapted to support the X-ray cassette.

10. The patient support apparatus of claim 9, wherein the support tray comprises a third actuator coupled to a bottom of the base member and in communication with the controller.

11. The patient support apparatus of claim 10, wherein the support tray comprises a third threaded lead screw coupled to the third actuator.

12. The patient support apparatus of claim 11, wherein the support tray comprises a clamp threadably coupled to the third threaded lead screw to move and engage and disengage the X-ray cassette.

13. The patient support apparatus of claim 8, wherein the support tray comprises one or more cassette sensors in communication with the controller.

14. The patient support apparatus of claim 13, wherein the controller is configured to determine a size of the X-ray cassette loaded on the support tray using the one or more cassette sensors.

15. The patient support apparatus of claim 1, wherein the one or more patient position sensors comprise at least one of ultrasonic sensors, laser sensors, and distance sensors.

16. The patient support apparatus of claim 15, wherein the controller includes a processor configured to activate the X-ray cassette mover and position the X-ray cassette relative to the patient.

17. The patient support apparatus of claim 16, wherein the controller uses data from the one or more patient position sensors to calculate a position of the patient relative to the frame.

18. A method of automatically moving an X-ray cassette with an X-ray cassette mover into an operational position relative to a patient on a patient support apparatus, said method comprising the steps of:

feeding the X-ray cassette into the X-ray cassette mover and loading the X-ray cassette on a support tray of the X-ray cassette mover;

determining the size of the X-ray cassette loaded on the support tray using a controller configured to utilize data from sensors on the support tray;

engaging the X-ray cassette with a clamp;

approximating, with the controller, a location of the patient on the patient support apparatus relative to an x-axis of an x-y coordinate system by comparing measurements taken by sensors on the patient support apparatus and approximating an x-dimension location of the patient;

approximating, with the controller, a location of the patient on the patient support apparatus relative to a y-axis of the x-y coordinate system by detecting a width of the patient with the sensors on the patient support apparatus and comparing measurements to a look-up table that correlates widths to the patient and approximating a y-dimension location of the patient; and moving the support tray and X-ray cassette, by operating the X-ray cassette mover using the controller, to a desired position under the patient to image the patient.

* * * * *